United States Patent [19]

Okawa et al.

[11] Patent Number: 5,493,039
[45] Date of Patent: Feb. 20, 1996

[54] METHOD FOR THE PREPARATION OF METHACRYLOXYPROPYLDIMETHYL-CHLOROSILANE

[75] Inventors: Tadashi Okawa; Shuji Yamada, both of Chiba Prefecture, Japan

[73] Assignee: Dow Corning Toray Silicone Co., Ltd., Tokyo, Japan

[21] Appl. No.: 502,951

[22] Filed: Jul. 17, 1995

[30] Foreign Application Priority Data

Jul. 18, 1994 [JP] Japan .................................. 6-187844

[51] Int. Cl.$^6$ .................................................. C07F 7/08
[52] U.S. Cl. ................................................. 556/440
[58] Field of Search .............................................. 556/440

[56] References Cited

U.S. PATENT DOCUMENTS

| | | | |
|---|---|---|---|
| 3,746,734 | 7/1973 | Berger et al. | 556/440 |
| 4,558,111 | 12/1985 | Tolentino | 556/440 X |
| 4,780,555 | 10/1988 | Bank | 556/440 |
| 4,946,977 | 8/1990 | Bernhardt et al. | 556/440 |
| 5,117,027 | 5/1992 | Bernhardt et al. | 556/440 |
| 5,145,979 | 9/1992 | Takatsuna et al. | 556/440 |
| 5,262,555 | 11/1993 | Okawa et al. | 556/440 |

FOREIGN PATENT DOCUMENTS

| | | |
|---|---|---|
| 1246289 | 10/1989 | Japan . |
| 5301881 | 11/1993 | Japan . |

OTHER PUBLICATIONS

Polymerization of Poly(dimethylsiloxane) macromers: 1. Copolymerization with styrene, vol. 26, pp. 437–442, Mar. 1985.

*Primary Examiner*—Paul F. Shaver
*Attorney, Agent, or Firm*—Sharon K. Severance

[57] ABSTRACT

The instant invention pertains to a method for the preparation of methacryloxypropyldimethylchlorosilane that is very efficient, yields a very pure methacryloxypropyldimethylchlorosilane, and produces little alpha-methylpropionyloxypropyldimethylchlorosilane impurity.

The instant invention comprises the addition reaction between allyl methacrylate and dimethylchlorosilane in the presence of hydrosilylation catalyst, wherein the water content of the allyl methacrylate does not exceed 200 ppm.

18 Claims, No Drawings

METHOD FOR THE PREPARATION OF METHACRYLOXYPROPYLDIMETHYL-CHLOROSILANE

BACKGROUND OF THE INVENTION

Methacryloxypropyl-functional organosilicon compounds readily copolymerize with radically polymerizing monomers such as methyl methacrylate and styrene. For this reason they are often used as starting materials for copolymers and as modifiers for polymers prepared from the polymerizing monomers. Among the methacryloxypropyl-functional organosilicon compounds, methacryloxypropyldimethylchlorosilane is typically employed as an endblocker or terminating agent for methacryloxy-functional silicone macromonomers. Methacryloxypropyldimethylchlorosilane is generally prepared by an addition reaction between allyl methacrylate and dimethylchlorosilane followed by isolation by distillative purification of the reaction product (see *Polymer*, Volume 26, page 437, 1985). One drawback that has generally been associated with this method is the pronounced tendency for gelation to occur during the reaction and distillative purification. Another drawback to this method has appeared when its methacryloxypropyldimethylchlorosilane product is used as an endblocker for methacryloxy-functional silicone macromonomers. Specifically this drawback is the frequent occurrence of low copolymerization conversions with radically polymerizing vinylic organic compounds.

It has now been found that alpha-methylpropionyloxypropyldimethylchlorosilane is produced as an impurity in the methacryloxypropyldimethylchlorosilane and that this impurity causes the reduced copolymerization conversions with radically polymerizing vinylic organic compounds. It has been also found that the production of the alpha-methylpropionyloxypropyldimethylchlorosilane impurity can be substantially reduced by reducing the water content in the starting allyl methacrylate to the maximum extent possible.

Therefore, it is an object of the instant invention a method for the preparation of methacryloxypropyldimethylchlorosilane that is very efficient, yields a very pure methacryloxypropyldimethylchlorosilane, and produces little alpha-methylpropionyloxypropyldimethylchlorosilane impurity.

SUMMARY OF THE INVENTION

This invention relates to a method for the preparation of methacryloxypropyldimethylchlorosilane that is very efficient, yields a very pure methacryloxypropyldimethylchlorosilane, and produces little alpha-methylpropionyloxypropyldimethylchlorosilane impurity. The method of the instant invention comprises reacting an allyl methacrylate containing less than 200 ppm water and a dimethylchlorosilane in the presence of hydrosilylation catalyst.

THE INVENTION

The instant invention relates to a method for the preparation of methacryloxypropyldimethylchlorosilane by an addition reaction between allyl methacrylate and dimethylchlorosilane in the presence of hydrosilylation catalyst, wherein the water content of the allyl methacrylate does not exceed 200 ppm.

The water content in the allyl methacrylate used in the instant invention must not exceed 200 ppm and preferably does not exceed 180 ppm. The allyl methacrylate containing less than 200 ppm water can generally be prepared by subjecting a commercial allyl methacrylate to a dehydration treatment. Any dehydration treatment can be used for this purpose as long as the allyl methacrylate is not reacted or modified by the treatment and the treatment has no adverse effects on the ensuing addition reaction.

The following dehydration methods are preferred for their simplicity and economics: (i) azeotropic dehydration by heating with a water-immiscible organic solvent, and (ii) use of a dehydrating agent such as molecular sieve, sodium sulfate, and others. These methods can reduce the water content in allyl methacrylate to 200 ppm or less. For the azeotropic dehydration, the water-immiscible organic solvent is preferably n-hexane, n-heptane, cyclohexane, and others. These organic solvents are preferred for several reasons. First, because they lack functional groups they will not negatively affect the ensuing addition reaction. Second, they have optimal boiling points, which results in suppression of methacryloxypropyl group polymerization during the azeotropic dehydration while at the same time making possible a satisfactory reaction rate in the ensuing addition reaction.

The water content in allyl methacrylate can be measured for the present purposes by the Karl Fischer method, which is a well-known method for determining the water content of organic compounds. This method uses the Karl Fischer reagent as an analytical reagent for the determination of water.

In the method of the instant invention, the allyl methacrylate: dimethylchlorosilane mixing ratio is not crucial. However, it is preferred to use larger allyl methacrylate: dimethylchlorosilane molar ratios since this produces increasingly less alpha-methylpropionyloxypropyldimethylchlorosilane impurity. As a result, allyl methacrylate: dimethylchlorosilane molar ratios of 1:1 to 3:1 are preferred, while the range of 1.1:1.0 to 2.0:1.0 is particularly preferred based on economic efficiency.

Transition metal catalysts from Group VIII of the Periodic Table are preferred for use as the hydrosilylation catalyst in the method of the instant invention. Among these Group VIII metal catalysts the platinum-based catalysts are the most preferred. The platinum-based catalysts are exemplified by alcohol solutions of chloroplatinic acid, platinum-olefin complexes, and complexes between chloroplatinic acid and vinyl-containing siloxanes. The catalyst should be added in a quantity that induces development of the addition reaction, and as a general rule is used at 0.01 to 100 ppm based on the total weight of the allyl methacrylate and dimethylchlorosilane.

It is preferred to add a polymerization inhibitor to the reaction system in order to inhibit the methacryloxypropyl group polymerization that occurs as a side reaction during the addition reaction between the allyl methacrylate and dimethylchlorosilane. Said polymerization inhibitor may be exemplified by, but not limited to, phenothiazine, hindered phenol compounds, amine compounds, and quinone compounds. The type and quantity of polymerization inhibitor are not crucial as long as its addition does not hinder development of the addition reaction and does inhibit methacryloxypropyl group polymerization. A beta-diketone compound, for example, acetylacetone, benzoylacetone, dibenzoylmethane, and so forth, may be added as taught in Japanese Patent Application Laid Open [Kokai or Unexamined] Number Hei 5-301881 [301,881/1993].

The method of the instant invention may be run under solventless conditions or may be run in the presence of a solvent. Solvents useful in the instant invention may be exemplified by, but not limited to aromatic hydrocarbons such as benzene, toluene, xylene, and others; aliphatic hydrocarbons such as hexane, heptane, cyclohexane, and others; ethers such as tetrahydrofuran, diethyl ether, and others; ketones such as acetone, methyl ethyl ketone, and others; and esters such as ethyl acetate, butyl acetate, and others. This solvent may be the same as or may differ from the organic solvent used during azeotropic dehydration of the allyl methacrylate.

The method of the instant invention may be run at room temperature, but it is preferably run with heating in order to obtain good reaction rates. The general range for the reaction temperature is 30° C. to 100° C., while the preferred range is 40° C. to 80° C.

The methacryloxypropyldimethylchlorosilane produced by the addition reaction is preferably isolated by distillation of the addition reaction product. A polymerization inhibitor, as described above, may be added to the reaction system in order to inhibit the methacryloxypropyl group polymerization that occurs as a side reaction during this distillative purification. A metal halide may be added to this distillation to serve as a gelation inhibitor as described in U.S. Pat. No. 5,262,555 herein incorporated by reference for its teaching of these inhibitors. The metal halide may be exemplified by, but not limited to, the chlorides, bromides, and iodides of chromium, cobalt, nickel, germanium, zinc, tin, mercury, copper, iron, palladium, tungsten, silver, vanadium, molybdenum, ruthenium, platinum, antimony, bismuth, selenium, and tellurium. The distillation may be conducted according to well-known distillation methodologies, and distillation under reduced pressures will typically be employed.

The methacryloxypropyldimethylchlorosilane yielded by the method of the instant invention is characterized by an extremely low content of alpha-methylpropionyloxypropyldimethylchlorosilane impurity. This methacryloxypropyldimethylchlorosilane is useful, for example, as an endblocker or terminating agent in the preparation of methacryloxy-functional silicone macromonomers.

So that those skilled in the art can understand and appreciate the invention taught herein, the following examples are presented, it being understood that these examples should not be used to limit the scope of this invention found in the claims attached hereto.

In the following examples "%" refers to "weight %". The water content in the allyl methacrylate was measured by the Karl Fischer volumetric titration method in accordance with JIS K 0068. According to this titration method, the titration solvent was placed in a titration receptacle and rendered anhydrous by dripping in Karl Fischer reagent, and the allyl methacrylate was then added with dissolution. This was followed by titration with Karl Fischer reagent, and the water content was determined from titrant addition.

EXAMPLE 1

A commercial allyl methacrylate was obtained and the water content was measured at 2,194 ppm. 100 parts of this allyl methacrylate was allowed to stand for 24 hours at room temperature over 5 parts molecular sieve (Molecular Sieve 4A from Wako Junyaku Kabushiki Kaisha) as dehydrating agent. The water content of the resulting allyl methacrylate was measured at 171 ppm.

While operating in a nitrogen atmosphere, chloroplatinic acid/1,3-divinyltetramethyldisiloxane complex was mixed into a mixture of 44.1 g (349.2 mmol) of the dried allyl methyacrylate and 0.3 g phenothiazine in a sufficient quantity to provide 20 ppm platinum metal based on the weight of the allyl methacrylate. The resulting mixture was heated to 70° C. while stirring and a small amount of dimethylchlorosilane was added dropwise. After confirmation of the initiation of the addition reaction, a reaction was run by adding 30 g (317.5 mmol) dimethylchlorosilane dropwise while maintaining the temperature at 60° C. to 75° C. by adjusting the water or air cooling and stirring for 30 minutes. After first distilling the low boilers from the reaction product under reduced pressure at room temperature, a fraction at 91° C. to 96° C. was obtained by distillation at 1 mmHg. The results of various analyses confirmed this fraction to be methacryloxypropyldimethylchlorosilane. Analysis of this fraction by capillary gas chromatography (detector: FID, hereinafter abbreviated as capillary GC) and gas chromatography/mass spectroscopy (hereinafter abbreviated as GC/MS) confirmed that it contained 0.49% alpha-methylpropionyloxypropyldimethylchlorosilane as impurity.

EXAMPLE 2

A commercial allyl methacrylate was obtained and its water content was measured at 2,194 ppm. 100 parts of this allyl methacrylate was allowed to stand for 24 hours at room temperature over 5 parts molecular sieve (Molecular Sieve 4A from Wako Junyaku Kabushiki Kaisha) as dehydrating agent. The water content of the resulting allyl methacrylate was measured at 171 ppm.

While operating in a nitrogen atmosphere, chloroplatinic acid/1,3-divinyltetramethyldisiloxane complex was mixed into a mixture of 60.2 g (476.3 mmol) of the dried allyl methacrylate and 0.3 g phenothiazine in a sufficient quantity to provide 20 ppm platinum metal based on the weight of the allyl methacrylate. The resulting mixture was heated to 70° C. while stirring and a small amount of dimethylchlorosilane was added dropwise. After confirmation of the initiation of the addition reaction, a reaction was run by adding 30 g (317.5 mmol) dimethylchlorosilane dropwise while maintaining the temperature at 60° C. to 75° C. by adjusting the water or air cooling and stirring for 30 minutes. After first distilling the low boilers from the reaction product under reduced pressure at room temperature, a fraction at 91° C. to 96° C. was obtained by distillation at 1 mmHg. The results of various analyses confirmed this fraction to be methacryloxypropyldimethylchlorosilane. Analysis of this fraction by capillary GC and GC/MS confirmed that it contained 0.27% alpha-methylpropionyloxypropyldimethylchlorosilane as impurity.

COMPARATIVE EXAMPLE 1

An addition reaction was run as in Example 1, but in this case using the commercially available undehydrated allyl methacrylate (water content=2,194 ppm) in place of the dried allyl methacrylate containing 171 ppm water that was used in Example 1. A fraction was again obtained by distillative purification of the reaction product as in Example 1. The results of various analyses confirmed this fraction to be methacryloxypropyldimethylchlorosilane. Analysis of this fraction by capillary GC and GC/MS confirmed that it contained 1.2% alpha-methylpropionyloxypropyldimethylchlorosilane as impurity.

EXAMPLE 3

A commercial allyl methacrylate was obtained and its water content was measured at 2,194 ppm. While operating under a nitrogen atmosphere, 44.1 g (349.2 mmol) allyl methacrylate, 20 g n-hexane, and 0.3 g phenothiazine were mixed and this mixture was subjected to an azeotropic dehydration by heating under reflux for 1 hour. The water content of the resulting mixture was measured at 150 ppm.

Sufficient platinum/1,3-divinyltetramethyldisiloxane complex to provide 20 ppm platinum metal based on the weight of the allyl methacrylate was blended into the dried mixture. The resulting mixture was heated to 70° C. while stirring and a small amount of dimethylchlorosilane was added dropwise. After confirmation of the initiation of the addition reaction, a reaction was run by adding 30 g (317.5 mmol) dimethylchlorosilane dropwise while maintaining the temperature at 60° C. to 75° C. by adjusting the water or air cooling and stirring for 30 minutes. After first distilling the low boilers from the reaction product under reduced pressure at room temperature, a fraction at 91° C. to 96° C. was obtained by distillation at 1 mmHg. The results of various analyses confirmed this fraction to be methacryloxypropyldimethylchlorosilane. Analysis of this fraction by capillary GC and GC/MS confirmed that it contained 0.33% alpha-methylpropionyloxypropyldimethylchlorosilane as impurity.

EXAMPLE 4

A commercial allyl methacrylate was obtained and its water content was measured at 2,194 ppm. While operating under a nitrogen atmosphere, 60.2 9 (476.3 mmol) allyl methacrylate, 20 g n-hexane, and 0.3 g phenothiazine were mixed and this mixture was subjected to an azeotropic dehydration by heating under reflux for 1 hour. The water content of the resulting mixture was measured at 150 ppm.

Sufficient platinum/1,3-divinyltetramethyldisiloxane complex to provide 20 ppm platinum metal based on the weight of the allyl methacrylate was blended into the dried mixture. The resulting mixture was heated to 70° C. while stirring and a small amount of dimethylchlorosilane was added dropwise. After confirmation of the initiation of the addition reaction, a reaction was run by adding 30 g (317.5 mmol) dimethylchlorosilane dropwise while maintaining the temperature at 60° C. to 75° C. by adjusting the water or air cooling and stirring for 30 minutes. After first distilling the low boilers from the reaction product under reduced pressure at room temperature, a fraction at 91° C. to 96° C. was obtained by distillation at 1 mmHg. The results of various analyses confirmed this fraction to be methacryloxypropyldimethylchlorosilane. Analysis of this fraction by capillary GC and GC/MS confirmed that it contained 0.30% alpha-methylpropionyloxypropyldimethylchlorosilane as impurity.

EXAMPLE 5

A commercial allyl methacrylate was obtained and its water content was measured at 2,194 ppm. While operating under a nitrogen atmosphere, 1,375.0 g (10,869.6 mmol) allyl methacrylate, 618 g n-hexane, and 8.2 g phenothiazine were mixed and this mixture was subjected to an azeotropic dehydration by heating under reflux for 1 hour. The water content of the resulting mixture was measured at 150 ppm.

Sufficient platinum/1,3-divinyltetramethyldisiloxane complex to provide 20 ppm platinum metal based on the weight of the allyl methacrylate was blended into the dried mixture. The resulting mixture was heated to 70° C. while stirring and a small amount of dimethylchlorosilane was added dropwise. After confirmation of the initiation of the addition reaction, a reaction was run by adding 646.5 g (6,841.3 mmol) dimethylchlorosilane dropwise while maintaining the temperature at 60° C. to 75° C. by adjusting the water or air cooling and stirring for 30 minutes. After first distilling the low boilers from the reaction product under reduced pressure at room temperature, a fraction at 91° C. to 96° C. was obtained by distillation at 1 mmHg. The results of various analyses confirmed this fraction to be methacryloxypropyldimethylchlorosilane. Analysis of this fraction by capillary GC and GC/MS confirmed that it contained 0.36% alpha-methylpropionyloxypropyldimethylchlorosilane as impurity.

COMPARATIVE EXAMPLE 2

An addition reaction was run as in Example 5, but in this case using the commercially available undehydrated allyl methacrylate (water content=2,194 ppm) in place of the mixture (water content=150 ppm) of allyl methacrylate, n-hexane, and phenothiazine that was used in Example 5. At the point at which approximately one-half of the dimethylchlorosilane had been added dropwise, the reaction mixture thickened, lost its fluidity, and finally gelled.

The method according to the instant invention comprises the use of allyl methacrylate containing less than 200 ppm water in the preparation of methacryloxypropyldimethylchlorosilane by an addition reaction between allyl methacrylate and dimethylchlorosilane in the presence of hydrosilylation catalyst. As a result, the method according to the instant invention produces little alpha-methylpropionyloxypropyldimethylchlorosilane impurity and is able to efficiently produce a very pure methacryloxypropyldimethylchlorosilane. The method of the instant invention also exhibits a secondary stabilizing effect in that methacryloxypropyl group polymerization is inhibited even when the reaction and distillative purification are run using conditions under which methacryloxypropyl group polymerization would normally occur and the system would gel.

What is claimed is:

1. A method for the preparation of methacryloxypropyldimethylchlorosilane wherein said method comprises an addition reaction between allyl methacrylate and dimethylchlorosilane in the presence of hydrosilylation catalyst, wherein the water content of said allyl methacrylate is less than 200 ppm.

2. A method as claimed in claim 1 wherein the water content of said allyl methacrylate is less than 180 ppm.

3. A method as claimed in claim 1 wherein the allyl methacrylate and dimethylchlorosilane are reacted at a molar ratio of 1:1 to 3:1.

4. A method as claimed in claim 3 wherein the allyl methacrylate and dimethylchlorosilane are reacted at a molar ratio of 1.1:1.0 to 2.0:1.0.

5. A method as claimed in claim 1 wherein the hydrosilylation catalyst is a Periodic Table Group VIII transition metal catalyst.

6. A method as claimed in claim 5 wherein the hydrosilylation catalyst is a platinum-based catalyst.

7. A method as claimed in claim 6 wherein the hydrosilylation catalyst is a complex between chloroplatinic acid and vinyl-containing siloxanes.

8. A method as claimed in claim 7 wherein the hydrosilylation catalyst is a platinum/1,3-divinyltetramethyldisiloxane complex.

9. A method as claimed in claim 1 wherein there is additionally present a polymerization inhibitor.

10. A method as claimed in claim 9 wherein the polymerization inhibitor is selected from the group consisting essentially of phenothiazine, hindered phenol compounds, amine compounds, and quinone compounds.

11. A method as claimed in claim 10 wherein the polymerization inhibitor is phenothiazine.

12. A method as claimed in claim 1 wherein there is additionally present during the addition reaction a solvent.

13. A method as claimed in claim 1 wherein the solvent is selected from the group consisting essentially of aromatic hydrocarbons, aliphatic hydrocarbons, ethers, ketones, and esters.

14. A method as claimed in claim 1 wherein the addition reaction is carried out at a temperature of 30° C. to 100° C.

15. A method as claimed in claim 14 wherein the addition reaction is carried out at a temperature of 40° C. to 80° C.

16. A method for the preparation of methacryloxypropyldimethylchlorosilane wherein said method comprises (I) an addition reaction between allyl methacrylate and dimethylchlorosilane in the presence of hydrosilylation catalyst, wherein the water content of said allyl methacrylate is less than 200 ppm; followed by (II) recovering the methacryloxypropyldimethylchlorosilane by distillation of the addition reaction product of (I) in the presence of polymerization inhibitor.

17. A method as claimed in claim 16 wherein the polymerization inhibitor is a metal halide.

18. A method as claimed in claim 17 wherein the metal halide is selected from the group consisting essentially of the chlorides, bromides, and iodides of chromium, cobalt, nickel, germanium, zinc, tin, mercury, copper, iron, palladium, tungsten, silver, vanadium, molybdenum, ruthenium, platinum, antimony, bismuth, selenium, and tellurium.

* * * * *